United States Patent
Littmann et al.

(10) Patent No.: US 8,269,495 B2
(45) Date of Patent: Sep. 18, 2012

(54) METHOD AND DEVICE TO DETERMINE AN INVERSION TIME VALUE OF TISSUE BY MEANS OF MAGNETIC RESONANCE TECHNOLOGY

(75) Inventors: Arne Littmann, Erlangen (DE); Peter Speier, Erlangen (DE); Katrin Christel Sprung, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 363 days.

(21) Appl. No.: 12/571,540

(22) Filed: Oct. 1, 2009

(65) Prior Publication Data

US 2010/0085051 A1 Apr. 8, 2010

(30) Foreign Application Priority Data

Oct. 1, 2008 (DE) .......................... 10 2008 050 030

(51) Int. Cl.
*G01V 3/00* (2006.01)
(52) U.S. Cl. ........................................ 324/309; 382/128
(58) Field of Classification Search .................. 324/309, 324/307, 306; 382/128, 174
See application file for complete search history.

(56) References Cited

U.S. PATENT DOCUMENTS

| | | | |
|---|---|---|---|
| 5,311,131 A * | 5/1994 | Smith ............................ | 324/309 |
| 5,999,839 A | 12/1999 | Hardy et al. | |
| 6,366,091 B1 | 4/2002 | Takahashi et al. | |
| 7,668,354 B2 * | 2/2010 | O'Donnell et al. ............ | 382/128 |
| 7,821,266 B2 * | 10/2010 | Feiweier ........................ | 324/309 |
| 7,835,783 B1 * | 11/2010 | Aletras .......................... | 600/413 |
| 2005/0245812 A1 | 11/2005 | Kim et al. | |
| 2005/0272997 A1 | 12/2005 | Grist et al. | |
| 2007/0009213 A1 | 1/2007 | Meadowcroft et al. | |
| 2007/0092131 A1 | 4/2007 | Guhring et al. | |
| 2007/0116339 A1 | 5/2007 | Shen | |
| 2008/0242973 A1 | 10/2008 | Warmuth | |

FOREIGN PATENT DOCUMENTS

JP    2004-024637 A    1/2004

OTHER PUBLICATIONS

"Bestimmung der Vitalität beim Myokardinfarkt," Huber et al. der Radiologe 44 (2004, pp. 146-151).

* cited by examiner

*Primary Examiner* — Louis Arana
(74) *Attorney, Agent, or Firm* — Schiff Hardin LLP

(57) ABSTRACT

In a method to determine an inversion time value for contrast improvement between different tissue in a contrast agent-supported magnetic resonance imaging, a series of magnetic resonance images of an imaging area is acquired using an inversion recovery sequence with different inversion times. A structure in the magnetic resonance images is segmented and a time response of the signal intensity of image elements corresponding to one another in the magnetic resonance images of the segmented structure is automatically determined. Minima of the signal intensity in the segmented structure are determined automatically and associated with the associated inversion time values. The optimal inversion time value for contrast improvement is automatically determined from the inversion time values that have been associated with the minima of the signal intensity in the segmented structure.

12 Claims, 4 Drawing Sheets

METHOD AND DEVICE TO DETERMINE AN INVERSION TIME VALUE OF TISSUE BY MEANS OF MAGNETIC RESONANCE TECHNOLOGY

BACKGROUND OF THE INVENTION

1. Field of the Invention

The present invention relates to a method for determining an inversion time value of tissue using magnetic resonance technology, as well as to a magnetic resonance apparatus for implementing such a method.

2. Description of the Prior Art

In recent years, contrast agent-supported tissue characterization by means of magnetic resonance technology has found increasing distribution in clinical practice. Conclusions about the extent and degree of damage in undernourished tissue or, respectively, after infarcts can be obtained with the aid of contrast agent-supported magnetic resonance examinations.

The basic principle of contrast agent-supported magnetic resonance imaging for tissue characterization utilizes the kinetics of a contrast agent based on gadolinium in tissue. In infracted, necrotic or scarred tissue, the contrast agent enrichment takes significantly longer than in healthy tissue due to the poor perfusion. A hyper-intense depiction of poorly perfused tissue thereby ensues later and is maintained for up to 90 minutes after the contrast agent administration. The region of the diseased tissue can thus be very precisely delimited. A demarcation between dysfunctional but still vital tissue and infarcted tissue is also possible.

To control the contrast between healthy and diseased tissue, the inversion recovery (IR) magnetization method is used in the magnetic resonance sequences for imaging. In the inversion recovery sequence, the contrast between healthy and damaged or, respectively, undernourished tissue predominantly depends on the T1 relaxation time. In an inversion module activated before the actual imaging sequence, a preparation pulse or 180° radio-frequency pulse inverts the longitudinal magnetization. The transversal magnetization thereby remains equal to zero. During the subsequent repetition, the negative longitudinal magnetization decays to zero and then rises again. Since no transversal magnetization can be created, no signal is measured either. In order to be able to generate a magnetic resonance signal, the longitudinal magnetization must be converted into a transversal magnetization via a subsequent excitation pulse, for example a 90° excitation pulse.

One measurement parameter in this sequence is the point in time between the inversion pulse and the excitation pulse; it is called the inversion time TI. The contrast between different tissue types is set with the inversion time TI. However, there is no standard value for the inversion time TI that always allows an optimal contrast distribution of the different tissue types. Normally, the contrast is controlled so that normal and healthy tissue is suppressed in the image presentation, thus is shown dark.

An important application field of the inversion recovery sequence is the vitality examination of heart tissue and the characterization of heart tissue, thus of the heart muscle or myocardium.

In magnitude images, as was already mentioned above the contrast very strongly depends on the correct setting of the inversion time TI. Here the optimal setting has until now been determined with the aid of a TI scout measurement method. The TI scout measurement uses a CINÉ sequence in which an inversion pulse is radiated at a trigger point in time. The different acquired heart phases have different time intervals relative to this pulse. The time interval of the individual images from the trigger point in time is thereby identical to the inversion time TI. After the end of the acquisition, the user then visually assesses in which image the healthy myocardium is shown darkest. The time interval between the trigger point in time and the measured heart phase that belongs to this image corresponds to the optimal TI value for the magnitude images.

The visual evaluation of the CINÉ image sequence for the selection of the optimal TI value as well as a subsequent manual translation of this value into the actual measurement sequence can contain errors. An incorrect or suboptimal TI value may be selected, and the translation of this value into the measurement sequence may be incorrect.

In the late enhancement technique that is implemented approximately 10 to 30 min after a contrast agent administration, the image acquisition in principle always ensues in the same heart phase. The inversion module is then activated variably before the image acquisition, corresponding to the variation of the inversion times.

The individual determination of the optimal TI value is superfluous if TI-independent pulse sequences are used, for example the PSIR (Phase Sensitive Inversion Recover) sequence. In addition to the image data, an additional echo is read out with a small flip angle. This echo is measured in the following heart beat. In a wider scope, the image contrast is therefore independent of the precise selection of the inversion time value. However, in spite of this many users want to use the optimal inversion time in the magnetic resonance image acquisition in order to have the generally accepted magnitude image present in addition to the finding.

A method for segmentation of the myocardium in real-time magnetic resonance image series is described in United States Patent Application Publication No. 2007/0116339 A1. A Hough transformation for approximation of limits of a structure shown in the image is thereby used.

United States Patent Application Publication No. 2007/0092131 A1 discloses a method with which the center point of a point-symmetrical structure is determined. A threshold selection method based on a greyscale histogram is thereby applied.

SUMMARY OF THE INVENTION

An object of the present invention is to provide a method and a device to determine an optimal inversion time value.

This object is achieved in accordance with the invention by a method to determine an inversion time value for contrast improvement between different tissue in a contrast agent-supported magnetic resonance imaging, wherein a series of magnetic resonance images of an imaging area by means of an inversion recovery sequence with different inversion times, a structure in the magnetic resonance images is segmented; a time response of the signal intensity of image elements corresponding to one another in the magnetic resonance images of the segmented structure is automatically determined; minima of the signal intensity in the segmented structure are automatically determined; and the optimal inversion time value for contrast improvement is automatically determined from the inversion time values which have been associated with the minima of the signal intensity in the segmented structure.

As before, the user activates the TI scout measurement. With the method according to the invention, the optimal inversion time value for the respective application is then automatically determined and can be automatically adopted in the following measurement sequences. Incorrect measurements based on individual assessments of the user are avoided. The selection of the optimal inversion time value is independent of the user. Input errors in the manual transfer of the inversion time value for the subsequent measurement protocols can also be avoided. Repeat measurements due to incorrect first measurements are no longer required, and the danger to the patient of having to remain in the magnetic resonance apparatus longer due to multiple measurements no longer exists.

Since the determination of the optimal inversion time is executed automatically, it can be implemented more often given longer measurement series. Today a change of the required inversion time value is often only roughly estimated given long measurement series.

Various criteria can be used to determine the optimal inversion time value from the established inversion time values of the image series. For example, the inversion time value at which the majority of the healthy myocardium pixels or myocardium voxels have their signal minimum can be taken as an optimal inversion time value.

In an embodiment, the inversion time value that belongs to the magnetic resonance image with the signal minimum occurring latest is taken as an optimal inversion time value.

In another embodiment, the series of magnetic resonance images ensues by means of a CINÉ measurement. In the CINÉ measurement, an inversion pulse is sent at the beginning of the RR interval in the cardiac cycle. The cardiac phases acquired with this protocol have different time intervals from the inversion pulse. The time interval of the individual images from the trigger point in time that is defined by the R-spike in the electrocardiogram is thereby identical with the inversion time value of a single, however, cardiac phase measurement sequence. It is advantageous that many images with different inversion time can be generated per time unit or per cardiac phase. The trade-off for this, however, is that dynamically altered contours must be evaluated in the image series. Additionally, a contrast loss can result if the flip angles are large enough because then no free relaxation is present.

In a further embodiment, the series of magnetic resonance images is acquired by using a late enhancement measurement. The inversion times are established by the interval of the inversion module from the actual image acquisition sequence. Since the late enhancement measurement always ensues in the same cardiac phase, no significant heart movement is contained in the image data. The segmentation of the structure to be examined is therefore particularly simple.

An additional advantageous embodiment is characterized in that a parameterizable model of the time response of the relaxation of the longitudinal magnetization of one of the different tissues (advantageously the healthy tissue) is used for segmentation. The model is adapted to the current temporal signal curve in that the free parameter of the model is determined so that, for example, the difference between the observed signal intensity and the signal intensity of the parameterized relaxation model is minimal. In this way it is possible to stably estimate the relaxation response based on only a few acquired images, such that a considerable amount of measurement time can be saved.

In a further advantageous embodiment, the imaging area is a short-axis section of the heart. The short-axis section shows simple characteristic geometric structures that can be segmented well.

DESCRIPTION OF THE PREFERRED EMBODIMENTS

Figure 1:
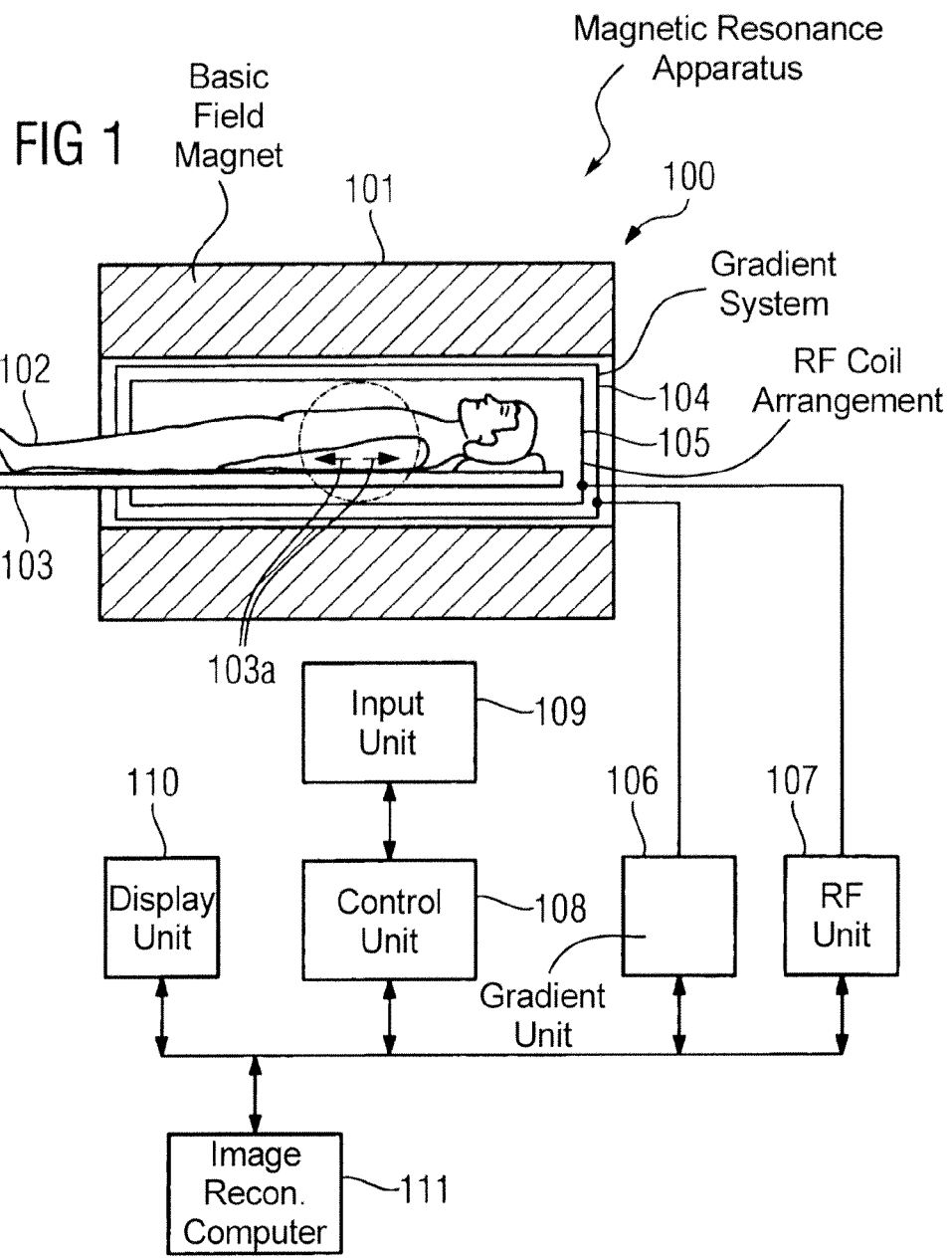
FIG. 1 schematically shows the basic design of a magnetic resonance apparatus.

FIG. 1 schematically shows a magnetic resonance apparatus 100 with which an inversion time value for contrast improvement between different tissue can be determined in a contrast agent-supported magnetic resonance image acquisition, for example for a following vitality examination of the heart muscle. Such a magnetic resonance apparatus 100 has a magnet 101 to generate a polarization field or basic magnetic field $B_0$. In the example shown here, the examination subject is an examination person 10 on a bed 103. As is schematically represented by arrows 103a, the bed 103 can be driven into the magnet 101 and be positioned therein for the examination of an organ. Furthermore, the magnetic resonance apparatus 100 has a gradient system 104 to generate magnetic field gradients that are used for imaging and spatial coding. To excite the polarization resulting in the basic magnetic field $B_0$, a radio-frequency (RF) coil arrangement 105 is provided that radiates a radio-frequency field into the examination person 10 in order to deflect the magnetization from the equilibrium state. To control the magnetic field gradients, a gradient unit 106 is provided; a radio-frequency unit 107 is provided to control the radiated radio-frequency pulses. A control unit 108 centrally controls the magnetic resonance apparatus 100; the selection of the imaging sequences likewise ensues in the control unit 108. An operator can select a sequence protocol via an input unit 109 and conduct additional adjustments at the magnetic resonance apparatus 100, for example the provision of imaging parameters. The sequence protocol defines the time sequence of the radio-frequency and gradient pulses to excite the image volume to be measured, for signal generation and for spatial coding. Each pulse sequence requires a repetition time that is optimized for the respective contrast. A display unit 110 serves to display acquired magnetic resonance signals or, respectively, reconstructed image data as well as the set parameters and other representations required to operate the magnetic resonance apparatus 100. Furthermore, a computer 111 is provided that, for example, serves for the reconstruction of image data from acquired magnetic resonance signals or to determine the inversion time (as is subsequently explained in detail). The general functionality of a magnetic resonance apparatus is known to those skilled in the art and thus a detailed description of the general components is not necessary herein.

The acquisition unit of the magnetic resonance apparatus 100 can include, for example, the gradient unit 106, the gradient system 104, the radio-frequency unit 107, the radio-frequency coil arrangement 105 and the magnet 101. Additional embodiments of the acquisition unit are naturally conceivable, for example the use of special head coils, breast coils and other local coil arrangements for radio-frequency transmission and reception operation, the use of different gradient coil sets for the gradient system and the use of different magnets, for example permanent magnets, normally-conducting or superconducting magnets. The control unit 108 controls the gradient unit 106 and radio-frequency unit 107 such that a first radio-frequency excitation pulse that generates a magnetization with known phase position is radiated into the examination region. The decay of the magnetization created by the excitation is likewise subsequently acquired with the aid of the radio-frequency pulse arrangement 105 and the radio-frequency unit 107. By activating the gradient unit 106, magnetic field gradients can be applied during these procedures, for example during the radiation of the radio-frequency pulses or during the acquisition of magnetic resonance signals. Magnetic field gradients can be applied with the gradient system 104 in different directions, for example for slice selection, phase coding or frequency coding, and thus serve as what are known as spoiler or crusher gradients that serve to destroy a remaining magnetization and the decay signal connected with this (free induction decay, FID). For example, a detected induction signal can be digitized by an analog-digital converter (not shown) and subsequently be processed by the computer 111.

To show dynamic processes in the body, for example the depiction of the heart movement, a periodic heart movement is subdivided into individual, successive cardiac phases. The image acquisition then ensues in a triggered manner across multiple cardiac periods until the number of measurement values that is necessary for the desired resolution is determined. The trigger signal is, for example, derived from the R-spike in the electrocardiogram. The images of the individual cardiac phases are then successively presented as a film workflow (ciné presentation) in a loop or back and forth. The observer receives the impression of seeing a video of the cardiac activity. The more phases that are shown, the better that the cardiac movement can be resolved.

For vitality examinations (for example of the heart muscle), contrast agent-supported imaging methods are also used. The special dynamic of the acquisition and subsequent flushing of the contrast agent from healthy and damaged tissue is thereby used for imaging. The contrast between healthy and damaged tissue is then further enhanced with inversion sequence modules before the actual imaging. Such sequences are called inversion recovery sequences. The inversion time (this is the time between the radio-frequency inversion pulse and the following radio-frequency excitation pulse) is advantageously selected so that healthy tissue does not emit a signal.

Figure 2:
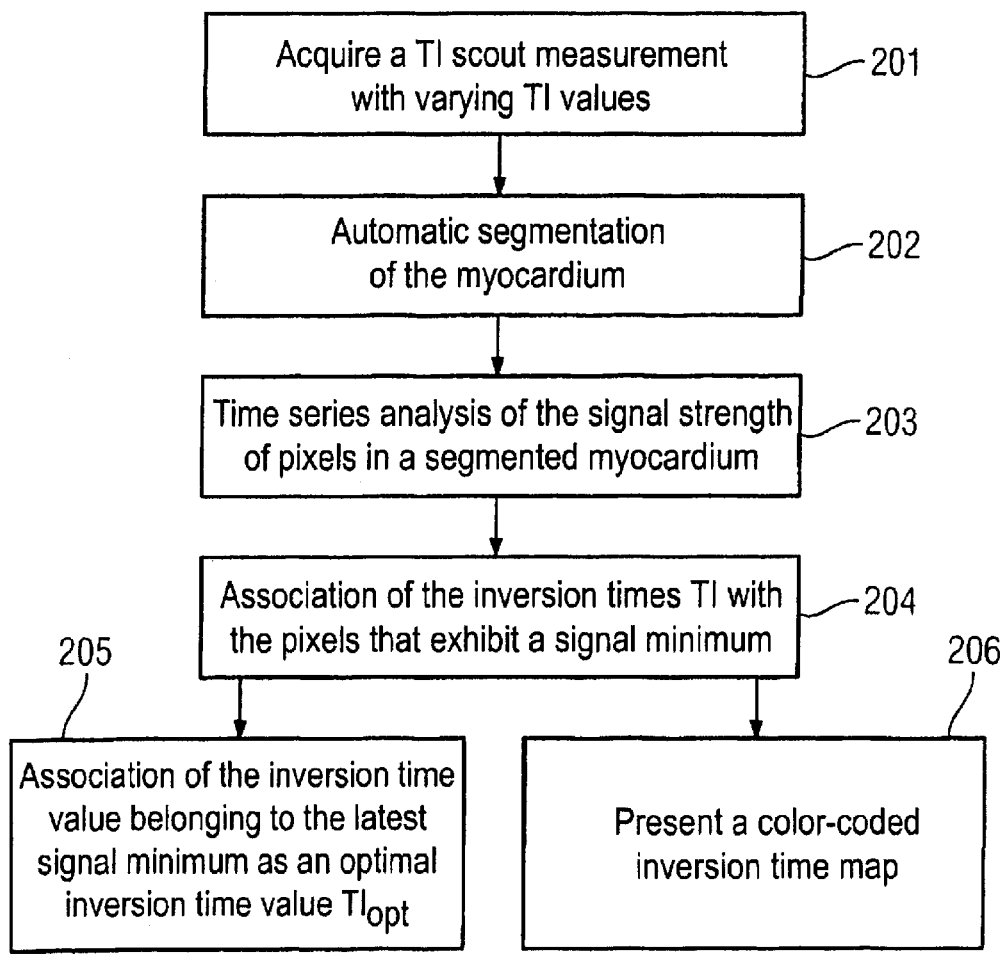
FIG. 2 shows basic steps of an exemplary embodiment of the method according to the invention.

FIG. 2 shows basic method steps of a first exemplary embodiment of the invention for the characterization of heart tissue. After a contrast agent injection with a contrast agent containing gadolinium, an image series of the imaging area (for example a short-axis section of the heart) is initially generated in a first method step 201 with an inversion recovery sequence. In the short-axis section, the left ventricle is shown as a circular area; the surrounding myocardium is represented as a circular ring. The image series is generated as an overview measurement with reduced resolution and is also designated as a TI scout measurement. Either a ciné measurement with subsequent segmentation of the heart muscle or a late enhancement measurement in which the heart muscle is subsequently only slightly segmented or is not segmented at all is applied here. In both measurements, the inversion time varies from image to image. In the CINÉ measurement, the inversion time results from the time interval of the R-spike from the point in time of the image acquisition of the cardiac phase; in the late enhancement measurement, the inversion module is variably set corresponding to the inversion time before the cardiac phase imaging, which essentially remains constant.

In the second method step 202, the cardiac muscle in the short-axis section is automatically segmented, as is described in detail further below. The automatic segmentation can start with already known regions (for example that have been defined in a data set generated from a preceding measurement), or can also start without start values. A ciné measurement to assist the segmentation could also be used. A segmentation of the myocardium in standard CINÉ data that have been acquired for a function analysis of the heart is thereby transferred to the inversion time overview measurement. This segmentation of the myocardium (what is known as an unmonitored segmentation) in standard ciné data is already a production technology.

In the third method step 203, all image elements or pixels within the segmented heart muscle are analyzed with regard to their signal intensities. In principle there are thereby two types of pixels that differ in terms of their relaxation response due to the contrast agent dynamic. Pixels that represent damaged tissue (for example scar tissue) will relax faster due to a higher contrast agent enhancement and therefore reach the signal zero crossing at an earlier inversion time after the inversion pulse than pixels that represent healthy tissue and possess a lower contrast agent enhancement.

In the fourth method step 204, the inversion time values belonging to the signal minimum or also the signal zero crossing are detected and associated with the corresponding pixels.

If, in the subsequent measurement, the healthy tissue should optimally not be shown, in a fifth method step 205 the signal zero crossing (and therefore the associated inversion time of the healthy heart muscle tissue) are determined. Due to the underlying contrast agent dynamic, this inversion time is the latest of all inversion time values of the signal minima. The optimal inversion time value $TI_{opt}$ for the subsequent imaging is thus taken by the pixels with the slowest relaxation.

In the sixth method step 206, a color coded inversion time map (TI map) can be generated to assist the user (and if necessary for individual adaptations of the sequence protocols) and be shown on the display unit 110.

In the seventh method step the optimal inversion time value $TI_{opt}$—thus the inversion time value at which healthy tissue generates no signal—is carried over to a subsequent imaging sequence to be implemented. The determined optimal inversion time value $TI_{opt}$ is then adopted into the following viability protocols automatically or after user confirmation.

It is still helpful to specify an indicator of the quality of the found inversion time value to the user. In the simplest case, this can be the underlying signal intensity curves. The possibility is therefore provided to detect dubious data and, if necessary, to repeat the measurement or to input a value by hand.

As was explained in the preceding using FIG. 2, to determine the optimal inversion time $TI_{opt}$ it is necessary to segment the healthy heart tissue and to subsequently implement a time series analysis of the signal curve in the healthy heart tissue. The segmentation and image analysis can be implemented with different methods, for example with active shape methods, image element-based methods or even cluster analysis methods.

In cluster analysis, multiple pixels are analyzed together. It is assumed that the relaxation response of the healthy heart tissue is spatially independent. Therefore, to determine the optimal inversion time value $TI_{opt}$ it is neither necessary to completely segment the healthy heart tissue in every image or to produce a spatial correspondence between the pixels in the images of the image series by means of a nonlinear image registration. Rather, it is sufficient to reliably identify somewhat healthy heart tissue in the acquired images in order to be able to analyze the temporal signal curve in the healthy heart tissue.

However, if it is desired to determine the relaxation response for every single pixel, a cluster analysis is unsuitable. Here pixel-based image analysis methods are used. With these a differentiation within the healthy and damaged heart tissue is additionally possible. Within an infarct area, regions affected with different severity can thus be differentiated. However, the spatial correspondence between the pixels in different images must thereby be established by means of a nonlinear image registration method. If the spatial correspondence is established, it is sufficient to identify the healthy heart tissue in a single image. The optimal inversion time value can then again be determined by an analysis of the temporal signal curve in the segmented area.

After a pixel-based image analysis, parametric maps for the parameters "Time until signal maximum" (TimeToPeak), "Time until signal minimum" (TimeToMin) or "Maximum signal slope" (MaxSlope) can also be generated and presented on the display unit 110.

Both cluster-based and pixel-based image analysis methods can be extended with a model of the relaxation response of the healthy heart tissue to increase stability and reduce the required measurement time. The model is to be adapted to the actual temporal signal curve in that its free parameters are determined so that, for example, the difference between the measured signal intensity and the signal intensity according to the relaxation model are minimal.

In all variants, the image segmentation can be initialized by means of previously conducted segmentation results.

Figure 3:
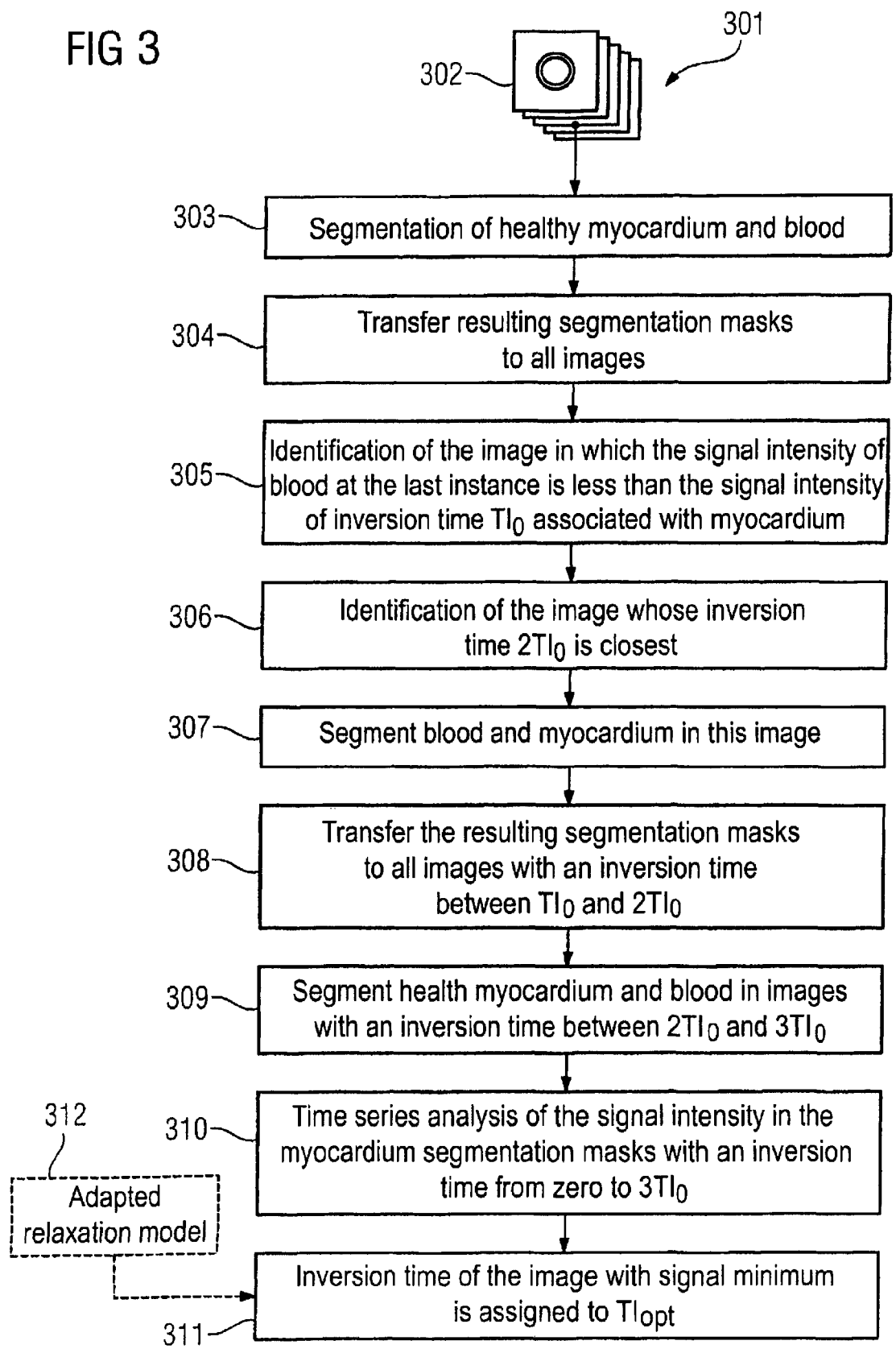
FIG. 3 shows relevant image processing steps of an exemplary embodiment for cluster analysis.

Using FIG. 3, an exemplary embodiment of the segmentation and determination of the optimal inversion time in which a cluster analysis is implemented is described for a ciné image series 301. In the last image (or frame) 302 of the image series 301, the (advantageously but not necessarily) healthy myocardium and blood are segmented in a first method step 303. Details regarding the segmentation are explained in detail further below using FIG. 4. The segmentation masks resulting from the segmentation 303 are then transferred to all images or frames of the ciné image series 301 in the method step 304. In the next method step 305, an image of the image series 301 is identified in which, with progressing inversion time, the signal intensity of blood becomes less than the signal intensity of the healthy myocardium. The inversion time connected with this image is designated in the following as $TI_0$. In the next method step 306, the image of the image series 301 is determined which possesses an inversion time that comes closest to the value $2TI_0$. In the following method step 307, healthy myocardium and blood in the image so determined are now segmented. The segmentation masks resulting from this are transferred in the next method step 308 to all images for which it applies that the inversion time lies between $TI_0$ and $2TI_0$. The reason for this method step 308 lies in that the contrast for an independent segmentation in this time period is possibly insufficiently high. In a further method step 309 blood and healthy myocardium are segmented in the images or frames for which the inversion time lies between $2TI_0$ and $3TI_0$. In the next method step 310, the time curve of the signal intensity within the myocardium segmentation masks is analyzed for the inversion times from zero to $3TI_0$. In a first variant 311, the optimal inversion time $TI_{opt}$ wherein the average signal intensity of the myocardium reaches its minimum is now determined from the image. In a second variant 312, a model of the relaxation response of the myocardium is adapted to the experimental observations. The optimal inversion time $TI_{opt}$ then results from a signal minimum in the model that is continuously adapted to the actual signal curve.

Figure 4:
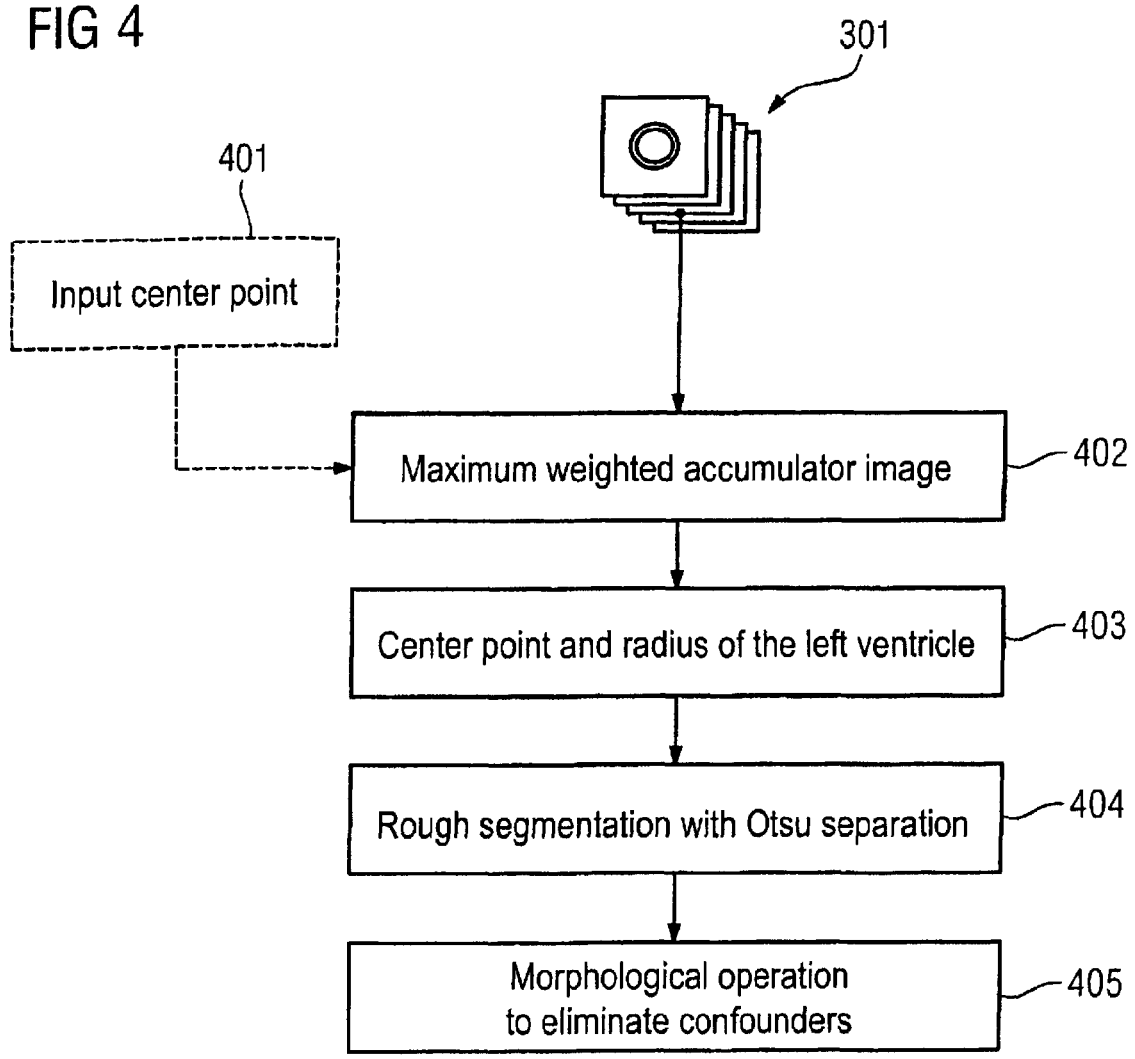
FIG. 4 shows an exemplary embodiment for segmentation of the healthy heart tissue.

The segmentation of the healthy myocardium in an image or frame of the image series 301 should now be explained using FIG. 4 in the example of the left ventricle. A distance-weighted Hough transformation is thereby implemented. In a first Step 401, a center point of the distance transformation is predetermined by a user. Alternatively, the center point of the image is adopted as a center point for the distance transformation. It is thereby assumed that the left ventricle is typically shown approximately in the center of the image. In the next method step 402, the maximum of an accumulator image of the Hough transformation weighted with the distance transformation is adopted as a center point of the left ventricle. The radius of the left ventricle results direction from the Hough transformation. Details regarding the Hough transformation are also found in United States Patent Application Publication No. 2007/0116339 A1, cited above. After carrying over these characteristic variables of the left ventricle in the method step 403, a rough segmentation of the healthy myocardium within the area found in the preceding (namely the circular disc resulting from the Hough transformation) ensues in the method step 403 by means of an Otsu separation with the assumption of two classes. The Otsu separation is described in United States Patent Application Publication No. 2007/0092131 A1, likewise cited above. In the next method step 405, potential confounders (for example air or sub-volume voxels or partial image elements) are eliminated from the rough segmentation of the healthy myocardium by means of morphological operations. The erosion method represents a morphological operation that is suitable for this purpose.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method to determine an inversion time value for contrast improvement between different tissue in contrast agent-supported magnetic resonance imaging, comprising the steps of:

with a magnetic resonance data acquisition unit, acquiring a series of magnetic resonance images of an imaging area using an inversion recovery sequence, with different inversion times, applied to an examination subject by the magnetic resonance data acquisition unit, each of said magnetic resonance images being comprised of image elements and each image element having a signal intensity associated therewith;

in a processor, segmenting a structure that appears in each of said magnetic resonance images;

in said processor, determining a time response of the signal intensity of image elements of the segmented structure that correspond to each other in the respective magnetic resonance images;

in said processor, determining minima of said signal intensity of said image elements in said segmented structure, and associating an inversion time value to said minima; and in said processor, determining an optimal inversion time value for contrast improvement for said segmented structure from said inversion time values associated with said minima, and making a signal representing said optimal inversion time value available at an output of said processor.

2. A method as claimed in claim 1 comprising, in said processor, determining said optimal inversion time value as an inversion time value associated with the magnetic resonance image in which the signal minimum occurs latest.

3. A method as claimed in claim 1 comprising acquiring said series of magnetic resonance images using a cine data acquisition sequence.

4. A method as claimed in claim 1 comprising acquiring said series of magnetic resonance images using a late enhancement data acquisition sequence.

5. A method as claimed in claim 1 comprising implementing said segmentation using cluster analysis.

6. A method as claimed in claim 1 comprising implementing said segmentation using an image element-based analysis.

7. A method as claimed in claim 1 comprising, in said processor, identifying a spatial correspondence of image elements in said segmented structure in the respective magnetic resonance images by implementing an image registration of said series of magnetic resonance images.

8. A method as claimed in claim 1 comprising, in said processor, using a parameterizable model of the relaxation time response for one of said different tissues in order to determine said signal minima.

9. A method as claimed in claim 1 comprising acquiring said series of magnetic resonance images as short-axis sections of the heart of the examination subject.

10. A method as claimed in claim 1 comprising, in said processor, generating a map representing a distribution of inversion time values in said segmented structure, and making said map available for display at said output of said processor.

11. A method as claimed in claim 1 comprising, in said processor, formulating said optimal inversion time as a parameter value in a magnetic resonance data acquisition sequence.

12. A magnetic resonance apparatus to determine an inversion time value for contrast improvement between different tissue in contrast agent-supported magnetic resonance imaging, comprising:

a magnetic resonance data acquisition unit that acquires a series of magnetic resonance images of an imaging area using an inversion recovery sequence, with different inversion times, applied to an examination subject by the magnetic resonance data acquisition unit, each of said magnetic resonance images being comprised of image elements and each image element having a signal intensity associated therewith;

a processor configured to segment a structure that appears in each of said magnetic resonance images;

said processor being configured to determine a time response of the signal intensity of image elements of the segmented structure that correspond to each other in the respective magnetic resonance images;

said processor being configured to determine minima of said signal intensity of said image elements in said segmented structure, and associating an inversion time value to said minima; and said processor being configured to determine an optimal inversion time value for contrast improvement for said segmented structure from said inversion time values associated with said minima, and to make a signal representing said optimal inversion time value available at an output of said processor.

\* \* \* \* \*